United States Patent
Irion et al.

(10) Patent No.: US 6,261,298 B1
(45) Date of Patent: Jul. 17, 2001

(54) DEVICE FOR CONCREMENT DESTRUCTION OR CRUSHING

(75) Inventors: Klaus Irion, Liptingen; Wolfgang Leibersperger, Tuttlingen, both of (DE)

(73) Assignee: Karl Storz-GmbH & Co. KG (DE)

( * ) Notice: Subject to any disclaimer, the term of this patent is extended or adjusted under 35 U.S.C. 154(b) by 0 days.

(21) Appl. No.: 09/506,532

(22) Filed: Feb. 17, 2000

(51) Int. Cl.$^7$ ................................................. H61B 17/22
(52) U.S. Cl. .............................................................. 606/128
(58) Field of Search .................................. 606/128, 127, 606/107, 167, 19, 22, 902, 170, 171, 184, 185

(56) References Cited

U.S. PATENT DOCUMENTS

| | | |
|---|---|---|
| 4,117,462 | 9/1978 | Miller . |
| 4,684,224 | 8/1987 | Yamashita et al. . |
| 4,976,524 | 12/1990 | Chiba . |
| 5,449,363 * | 9/1995 | Brust et al. ............................ 606/128 |
| 5,951,570 * | 9/1999 | Leibersperger et al. ............. 606/128 |

FOREIGN PATENT DOCUMENTS

| | | |
|---|---|---|
| 35 37 155A1 | 4/1986 | (DE) . |
| WO96/33661 | 10/1996 | (WO) . |

* cited by examiner

*Primary Examiner*—Pedro Philogene
(74) *Attorney, Agent, or Firm*—St. Onge Steward Johnston & Reens LLC

(57) ABSTRACT

A device for concrement destruction or crushing is disclosed which comprises an elongate probe adapted to be introduced into the human body, a drive unit that accelerates an impact body and a lever unit comprising at least one single-arm lever which is supported for rotation about an axis of rotation in such a way that it bears, in its home position, on the proximal end surface of the probe in particular, and which is rotated by the hitting impact body such that the lever accelerates the probe, which bears expediently against it, and the probe performs a translational movement causing the destruction or crushing of the concrement by the distal end surface of the probe hitting thereon. A distance ($r_3$) of the center of the bearing surface of the lever in its home position on the proximal end surface from said axis of rotation of the probe is shorter and preferably distinctly shorter than the distance ($r_1$) of the center of the impact area of the impact body on the lever from the axis of rotation, and that the ratio of the distances $r_1$ and $r_3$ is so selected that the probe will reach a maximum translational speed with a maximum transfer of energy from the impact body to the probe.

11 Claims, 2 Drawing Sheets

DEVICE FOR CONCREMENT DESTRUCTION OR CRUSHING

DESCRIPTION

1. Field of the Invention

The present invention relates to a device for concrement destruction or crushing in accordance with the introductory clause of Patent claim 1.

2. Prior Art

Devices for intracorporeal operation for concrement destruction or crushing have been commonly known. Such devices are used, for instance, as so-called lithotripters in medicine for destroying concrements such as renal calculi, urinary calculi or the like by short surge pulses of a probe introduced into the human body, or to comminute them to such a size that they can be discharged via the urinary tract.

A device which the wording of the introductory clause of Patent claim 1 starts out from is described in the document WO 96/33661. That device comprises an elongate probe adapted for being introduced into the human body, particularly via the ureter. A lever bears against the proximal end of the probe, which performs a rotating movement for accelerating the probe to perform, in its entirety, a translational movement at a sufficient rate such that when the distal end of the probe hits the concrement the latter will be crushed. The lever is driven, for instance, by means of an impact body which hits the lever with a high speed for driving it to perform a high-speed rotational movement.

From the European Patent EP 0 317 507 B1 an apparently similar device for concrement crushing is known. In that device a projectile hits the proximal interface of a wave It is intended that the hitting projectile should excite shock waves in the wave guide which are meant to result in a displacement of the distal interface of the wave guide.

In distinction from the device known from the European Patent EP 0 317 507 B1, the device known from the document WO 96133661, wherein merely or mainly shock waves or compression waves are excited in the wave guide, presents the following advantage: as with the device known from WO 96/33661 the probe is displaced as one unit the entire mass of the probe contributes to the kinetic energy of the probe. In the device known from the European Patent EP 0 317 507 B1, by contrast, only that fraction of the entire mass contributes to the kinetic energy which is influenced by the compression wave "migrating therethrough". As a result, the "effective kinetic energy" is much higher in the device known from WO 96/33661, where the probe is moved as a complete unit, so that an excellent crushing result is achieved.

The reason for the translational movement of the probe as a single unit, instead of the excitation of a shock wave or a compression wave, resides in the use of a lever:

The lever produces the effect of a transformation element achieving a low-pass effect. Due to this low-pass effect the kinetic energy of the impact body is transformed by the lever, which serves as transformation element, in such a way that substantially only a translational or uniform straight movement of the probe is achieved with the aforementioned high kinetic energy, without a therapeutically effective compression wave fraction.

BRIEF DESCRIPTION OF THE INVENTION

The present invention starts out from the finding that with an optimisation of the ratio of the distance of the bearing surface centre of the lever, which serves as transformation element in a home position on the proximal end surface of the probe, from the rotational axis, to the distance of the centre of the impact area of the impact body on the lever from the rotational axis it is possible to achieve a translational speed as high as possible at an optimum kinetic energy of the probe.

In particular, the present invention is based on the finding that in the device known from WO 96/33661 the lever ratios—as shown in the drawing—are not selected at an optimum.

The present invention is therefore based on the problem of proposing a device serving for mechanical concrement crushing, wherein the probe hits on the concrement at the maximum speed possible and wherein a maximum amount possible of kinetic energy of the impact body is transferred to the probe.

In accordance wit the invention, this problem is solved with the provisions that the distance of the centre of the bearing surface of the lever in its home position on the proximal end surface of the probe, from the rotational axis is smaller and particularly definitely smaller than the distance of the centre of the impact area of the impact body on the lever from the rotational axis, and that the ratio of the distance is so selected that the probe will achieve a maximum translational speed.

This means that the first impact point is located between the rotational axis and a freely mobile end of the lever arm, and that the probe is acted upon in particular by another area of the lever element rather than by the centre of the lever element. Whereas in the conventional lever design and lever arrangement, which are made in consideration of the cylindrical structure of the housing, the first impact point is provided on the freely mobile lever end and the second impact point is located precisely in the middle between the two lever ends, the inventive asymmetric position of the impact points permits the matching of the energy transfer from the impact body to the probe with the involved masses of the impact body, the lever and the probe, and makes it possible that losses in energy transfer, which are caused by the lever mechanism, will be largely avoided.

The lever may not only be a single-arm lever but fundamentally the most different types of transfer or transformation elements such as the arrangements of several levers may be selected which, due to different distances between the impact points and the rotational axes, i.e. on account of different impact radii, allow for matching the lever action with a maximum energy transfer to the impact probe.

With the optional application of a single-arm lever it is preferred that the distance of the centre of the bearing surface of the lever on the proximal end surface of the probe is wider than the distance between the centre of gravity of the lever and the rotational axis.

In particular, the rotational axis may be provided for displacement along the longitudinal axis of the lever in its home position so that the lever action can be adjusted. For an optimisation of the energy transfer not only in the zone of the interior of the housing but also between the distal probe end and the concrement a regulation of the lateral position of the lever element is expedient when the energy transfer for crushing concrements of different sizes should be harmonised with the respective concrement mass.

In an alternative or additionally it is possible that the proximal end of the impact probe and the impact unit are provided for lateral displacement relative to each other so as to permit a regulation of the lever action. Whilst a displacement of the lever varies both impact radii it is possible, in correspondence with this potential configuration, to optimise one of the impact radii independently of the other radius. In this context, the term "displacement" is to be understood here to denote any movement which results in a lateral dislocation of the probe and the impact unit, in opposition to the literal meaning otherwise common; for instance, a rotation of the impact unit or of the rear part of the housing, respectively, about an axis extending outside the centre of the housing or the proximal probe end, or any other adjusting mechanism may result in a lateral approximation of the impact unit and the impact probe (or their extensions on the housing side, respectively).

It is moreover possible that the lever element has a varying cross-section over its length. With this provision it is possible—either as an alternative of or in addition to the aforementioned provisions—to achieve a further matching of the energy transfer to the lever and from the lever to the probe.

Particularly when the mass of the lever is definitely smaller than the mass of the impact body and the mass of the lever corresponds roughly to half the mass of the impact body or less and the mass of the probe corresponds to twice the mass of the impact body or more approximately it is preferable that the following relationship applies for the distances r1 and r3, at least in approximation:

$$(r_3/r_1)^2 = m_1/m_3$$

wherein $m_1$ mass of the impact body $m_3$ mass of the probe $r_1$ distance of the centre of the impact area of the impact body on the lever from the axis of rotation $R_3$ distance of the centre of the bearing surface of the lever in its home position on the proximal end surface from the axis of rotation of the probe.

With this configuration the kinetic energy of the projectile is transferred to the probe practically completely, despite different masses of the probe and the impact body. As due to its length which is necessary for introduction into the human body the probe has mostly a distinctly heavier weight than the projectile a complete energy transfer can be achieved only with different impact radii of the impact unit and the probe.

On account of the lever speed which is proportional to the length of the lever arm, the aforementioned condition for the ratio corresponds to the energy preservation or the complete energy transfer to the probe, with the mass of the probe including, in the true sense of the word, also the masses of all parts that are moved during the impact process simultaneously with the probe.

In all other respects, the inventive device may be configured in the same manner as the unit described in WO 96/33661:

For instance, the drive unit may include a tube in which the impact body is accelerated, e.g. by means of compressed air or by means of solenoids.

Moreover, the drive unit may include at least one additional lever.

BRIEF DESCRIPTION OF THE DRAWING

The invention will be described in the following by exemplary embodiments, without any restriction of the general inventive idea, referring to the drawing which explicit reference is made to in all other respects as far as the disclosure of all inventive details is concerned which are not explained in more details in the text. In the drawing.

DESCRIPTION OF AN EMBODIMENT

Figure 1:
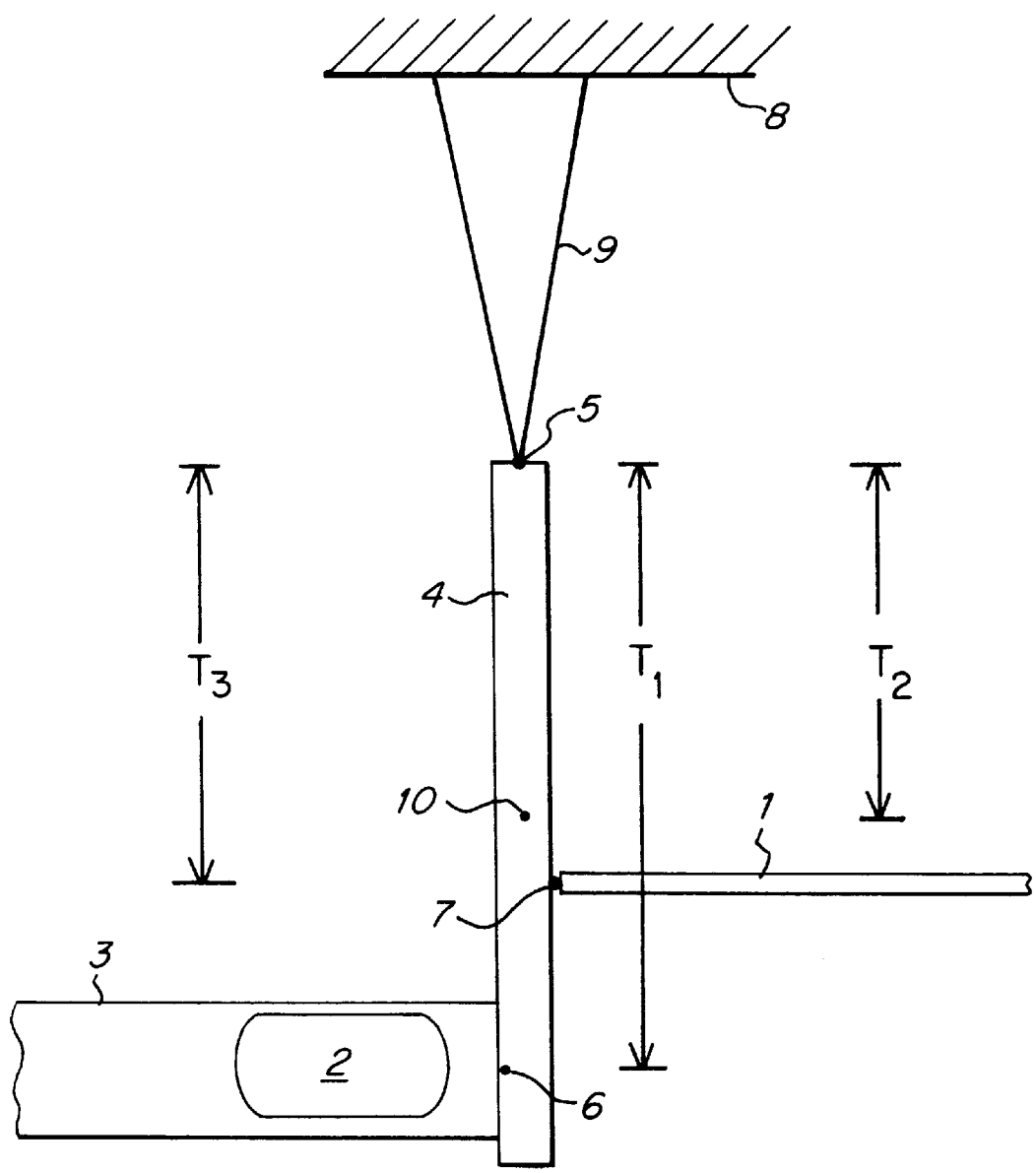
FIG. 1 is a schematic of an inventive lithotripter.

FIG. 1 shows an inventive device. The device comprises a probe 1 that may be introduced, for instance into the ureter, and which serves to destroy or crush a concrement in the body such as a urinary calculus. As is known from the document WO 96/33661, the probe is accelerated to a translational speed, which amounts to 5–10 m/s in a typical case, in the following manner:

An impact body 2 is accelerated in a tube 3, for instance by means of compressed air or by an electromagnetic field, to a comparatively high speed. The impact body 2 hits on a lever 4 which is rotatable about an axis 5 and which, in its home position, bears against the proximal end of the probe 1. The axis of rotation 5 is spaced by a defined distance by a holder 9 e. g. on the outside wall 8 of a handpiece.

The projectile 2, which is accelerated by the impact unit 3, hits against the lever 4 which acts upon the proximal end of the impact probe and thus transfers the kinetic energy of the projectile to the probe. With the lever, which has the function of a transformation element, a low-pass effect is achieved so that ultrasonic compression waves will not be excited. The probe rather performs practically a pure translational movement with a high kinetic energy, without the excitation of therapeutically effective compression waves in the probe. Insofar, the device is known from the document WO 96/33661.

$r_1$ denotes the distance between the centre 6 of the impact area of the impact body 2 on the lever 4 and the axis of rotation 5.

$r_2$ indicates the distance between the centre of gravity 10 of the lever 4 and the axis of rotation 5.

$r_3$ denotes the distance between the centre 7 of the bearing surface of the lever 4 in its home position on the proximal end surface 11 of the probe 1 and the axis of rotation 5.

In accordance with the invention, the ratio between the distances $r_1$ and $r_3$ is so selected that the probe will reach a maximum translational speed at a maximum of kinetic energy.

To this end the first impact point 6—in opposition to the device known from the aforecited prior art document—is not disposed directly on the freely mobile—in FIG. 1 lower-end of the lever; moreover the second impact point 7 may be arranged at an asymmetric offset in particular.

It is particularly preferable that the distance $r_3$ is longer than the distance $r_2$ of the centre of gravity 10 of the lever from the axis of rotation 5.

Figure 2:
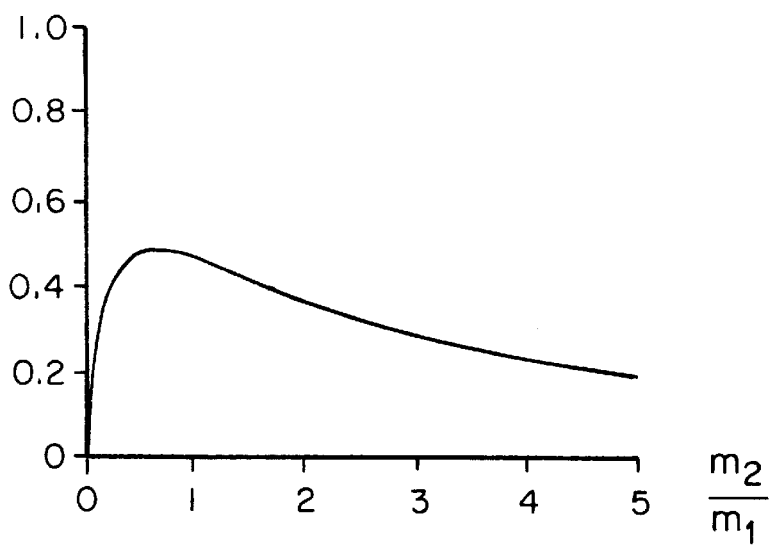
FIG. 2 is a graphic illustration of the energy transfer which can be achieved with conventional lithotripters for different probe sizes.
Figure 3:
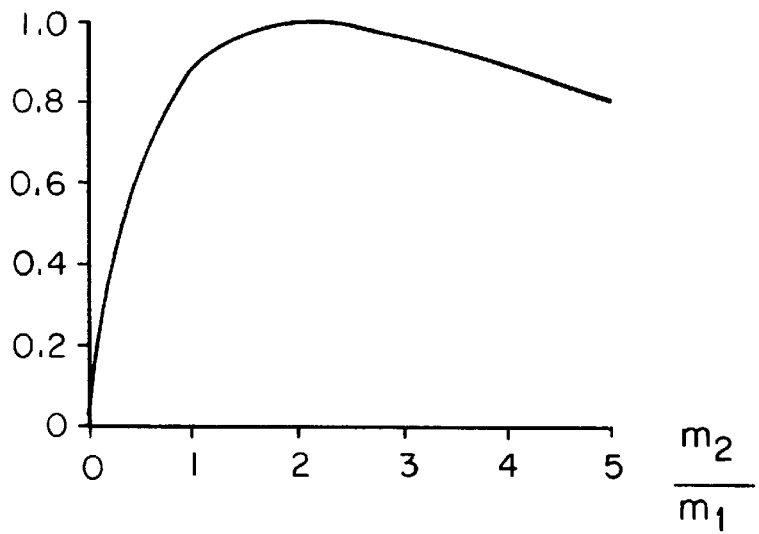
FIG. 3 is a graphic illustration of the energy transfer which can be achieved with the inventive lithotripter for different probe sizes.
Figure 4:
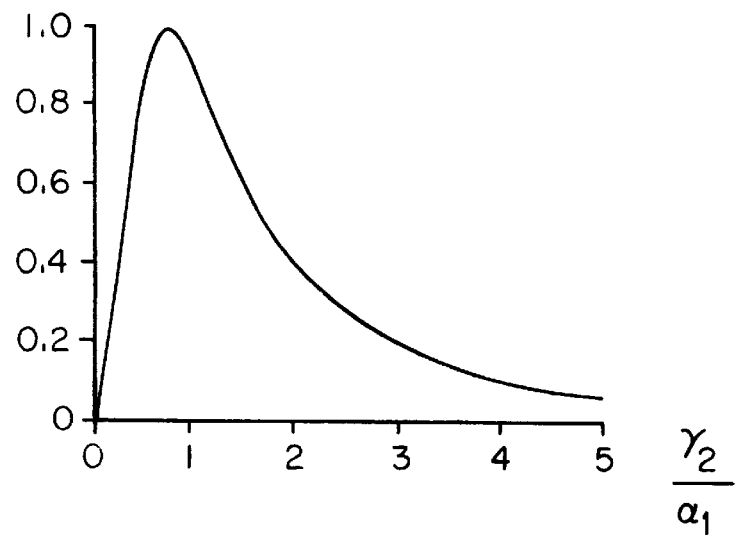
FIG. 4 is a graphic illustration of the energy transfer which can be achieved with the inventive lithotripter for different impact radii of the probe.

FIGS. 2, 3 and 4 illustrate the energy transfer conditions which can be achieved with known and inventive devices for intracorporeal lithotripsy.

FIG. 2 illustrates the energy transfer i.e. the ratio of the kinetic energy transferred by the impact probe relative to the energy of the projectile hitting on the lever, for probe masses $m_3$ from twice to five times the mass $m_1$ of the projectile.

Due to the lever mechanism of the conventional device, which is matched with the cylindrical shape of the housing, the kinetic energy of the projectile is transferred to the probe only incompletely even in the most favourable case of a probe weight of roughly 67% of the projectile mass.

FIG. 3 shows the energy transfer situation with the inventive lever mechanism for the same probe sizes, wherein the first impact radius $r_1$ is optimised for the mass ratio between the projectile and the lever whilst the impact radius $r_3$ is optimised for a probe having twice the weight of the projectile; in the case of a lever having a mass corresponding to half the mass of the projectile, for instance, both impact radii are shorter than half the length of the lever; as the probe is heavier than the projectile the impact radius $r_3$ is smaller than the impact radius $r_1$.

FIG. 4 shows the energy transfer as a function of the ratio of the impact radius $r_3$ to the impact radius $r_1$ with a first impact radius harmonised with the mass of the lever and with a probe having a mass twice the weight of the projectile, which reaches the maximum value of 1 like in FIG. 3.

From FIGS. 2 to 4 it is apparent that the asymmetric arrangement of the impact unit and the impact probe, which is proposed in accordance with the present invention, permits a practically complete transfer of energy to the impact probe relative to the lever, which cannot be achieved with conventional lithotripters provided with a lever mechanism, so that the efficiency of lithotripters in concrement crushing will be increased.

What is claimed is:

1. Device for concrement destruction or crushing, comprising
   an elongate probe (1) adapted to be introduced into the human body,
   a drive unit that accelerates an impact body (2), and
   a lever unit (4) comprising at least one single-arm lever which is supported for rotation about an axis of rotation (5) in such a way that it bears, in its home position, on the proximal end surface (11) of the probe in particular, and which is rotated by the hitting impact body such that the lever accelerates the probe, which bears against it, and the probe performs a translational movement causing the destruction or crushing of the concrement by the distal end surface (12) of the probe hitting thereon,
   characterised in that the distance ($r_3$) of the centre of the bearing surface of said lever in its home position on the proximal end surface (11) of the probe (1) from said axis of rotation (5) is shorter and particularly distinctly shorter than the distance ($r_1$) of the centre of the impact area of said impact body on the lever from said axis of rotation (5), and
   that the ratio of said distances $r_1$ and $r_3$ is so selected that the probe will reach maximum translational speed.

2. Device according to claim 1, characterised in that the distance $r_3$ is longer than the spacing $r_2$ of the centre of gravity (10) of said lever from said axis of rotation (5).

3. Device according to claim 1 characterised in that said axis of rotation (5) is displaceable along the longitudinal axis of said lever in its home position such that said distances $r_1$ and $r_3$ are adjustable.

4. Device according to claim 1, characterized in that the proximal end of said probe and the drive unit are displaceable relative to each other in a direction orthogonal on the longitudinal axis of said probe such that the lever ratios are adjustable.

5. Device according to claim 1, characterized in that said lever element has a cross-section varying over its length.

6. Device according to claim 1, characterized in that the mass ($m_2$) of said lever corresponds approximately to half the mass ($m_1$) of said impact body or less, and that the mass ($m_3$) of said probe amounts to roughly twice the mass of said impact body or more.

7. Device according to claim 6, characterised in that the following relationship applies, at least in approximation, for said distances $r_1$ and $r_3$:

$$(r_3/r_1)^2 = m_1/m_3$$

wherein
   $m_1$ mass of the impact body
   $m_3$ mass of the probe.

8. Device according to claim 1, characterized in that said drive unit comprises a tube (3) in which said impact body (2) is accelerated.

9. Device according to claim 8, characterised in that said impact body (2) is accelerated in said tube (3) by means of compressed air.

10. Device according to claim 8, characterised in that said impact body (2) is electromagnetically accelerated in said tube (3).

11. Device according to claim 1, characterized in that said drive unit comprises at least one additional lever.

* * * * *